United States Patent
Guy et al.

[11] Patent Number: 5,217,572
[45] Date of Patent: Jun. 8, 1993

[54] CENTRIFUGAL EVAPORATOR-CONCENTRATOR FOR CONCENTRATING SPECIMENS BY EVAPORATION OF THE SOLVENT

[75] Inventors: Jean L. Guy, Massy; Michel Serveau, Le Pecq, both of France

[73] Assignee: Jouan, Saint-Nazaire, France

[21] Appl. No.: 790,535

[22] Filed: Nov. 12, 1991

Related U.S. Application Data

[62] Division of Ser. No. 492,101, Mar. 12, 1990, Pat. No. 5,084,133.

[30] Foreign Application Priority Data

Mar. 20, 1989 [FR] France .................. 89 03627

[51] Int. Cl.⁵ .................................. B01D 1/00
[52] U.S. Cl. ......................... 159/6.1; 159/16.1;
 159/DIG. 16; 202/205; 203/DIG. 18; 422/72;
 422/101; 494/18; 494/26; 494/37; 494/61
[58] Field of Search .............. 159/6.1, 47.1, 16.1,
 159/8, 49, DIG. 16, 43.2, 44; 202/205; 203/49,
 91, DIG. 18; 494/13, 16, 17, 18, 25, 26, 37, 61;
 422/72, 101; 436/177; 210/781, 782

[56] References Cited

U.S. PATENT DOCUMENTS

| | | | |
|---|---|---|---|
| 529,663 | 11/1894 | Naylor | 494/26 |
| 3,274,756 | 9/1966 | Stern | 159/6.1 |
| 3,304,990 | 2/1967 | Ontko et al. | 494/61 |
| 3,327,938 | 6/1967 | Stallmann | 494/61 |
| 4,129,419 | 12/1978 | Hermann | 494/26 |
| 4,226,669 | 10/1980 | Vilardi | 494/61 |
| 4,244,513 | 1/1981 | Fayer et al. | 494/61 |
| 4,254,943 | 3/1981 | Bjorkman | 202/205 |
| 4,693,702 | 9/1987 | Carson et al. | 494/61 |
| 4,857,811 | 8/1989 | Barrett et al. | 494/26 |
| 5,137,604 | 8/1992 | Meeks et al. | 202/236 |

*Primary Examiner*—Wilbur Bascomb, Jr.
*Attorney, Agent, or Firm*—Larson and Taylor

[57] ABSTRACT

The centrifugal evaporator-concentrator includes a central tubular pivot (18) surmounted by a nozzle (35) and constituting the pivot axis of a rotor (9) rotating in a vessel (8) closed by a cover (11). With the rotor rotating in the partial vacuum created by a vacuum pump (33), a small quantity of gas or air is temporarily and periodically admitted into the vessel, this gas being heated by a heating resistor (38) inside the vessel for the purpose of heating by conduction the specimens to be concentrated and of accelerating the rate of evaporation.

14 Claims, 5 Drawing Sheets

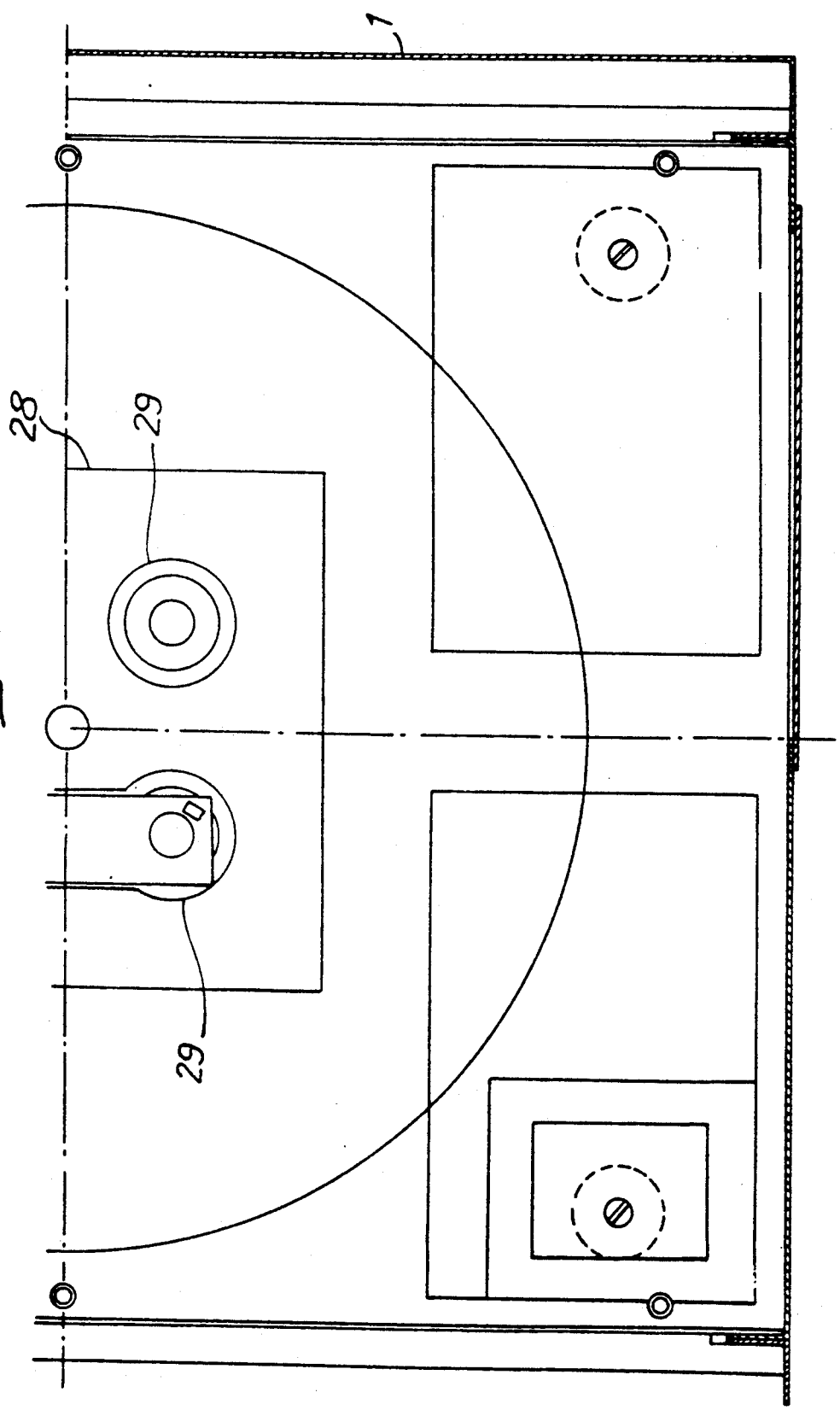

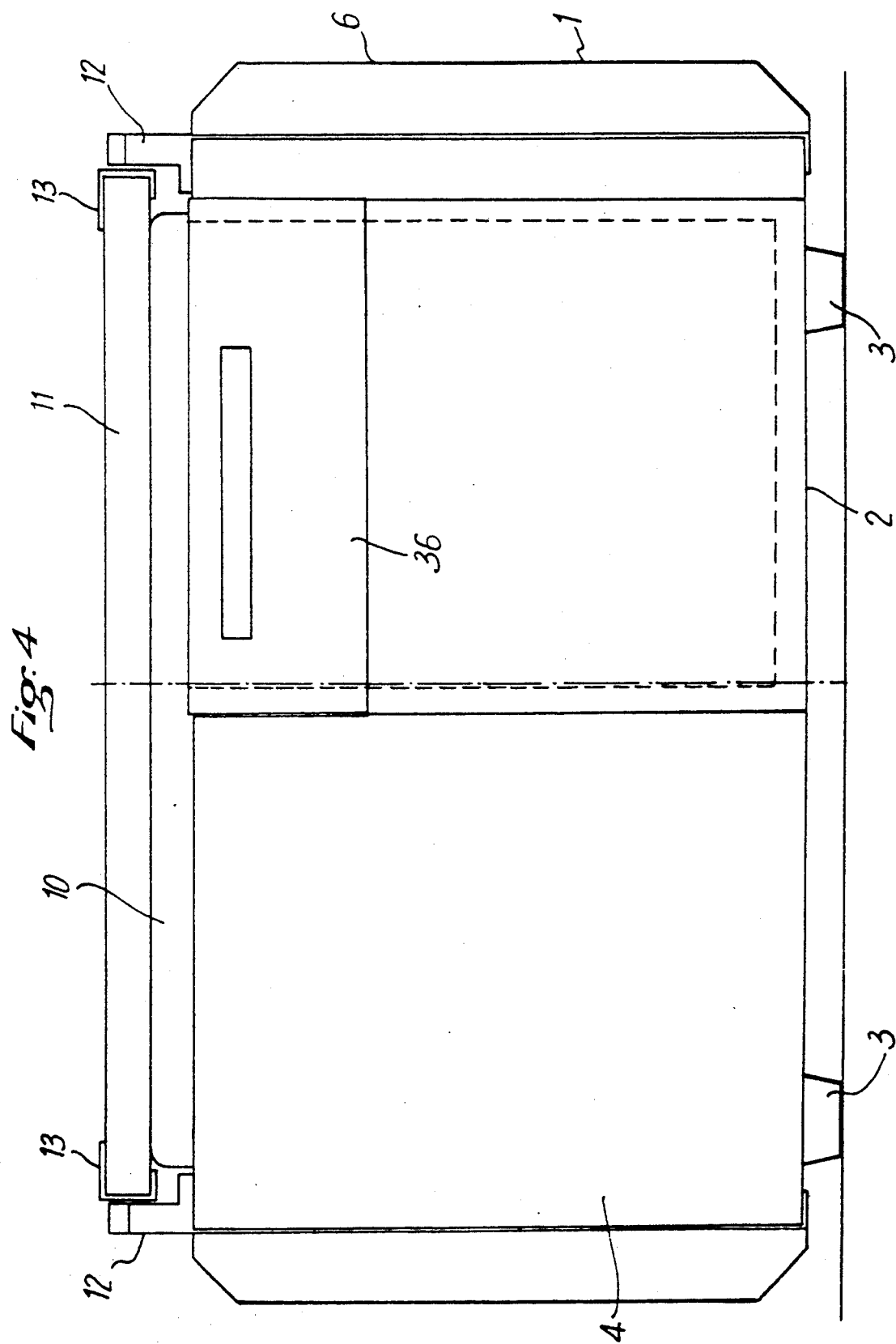

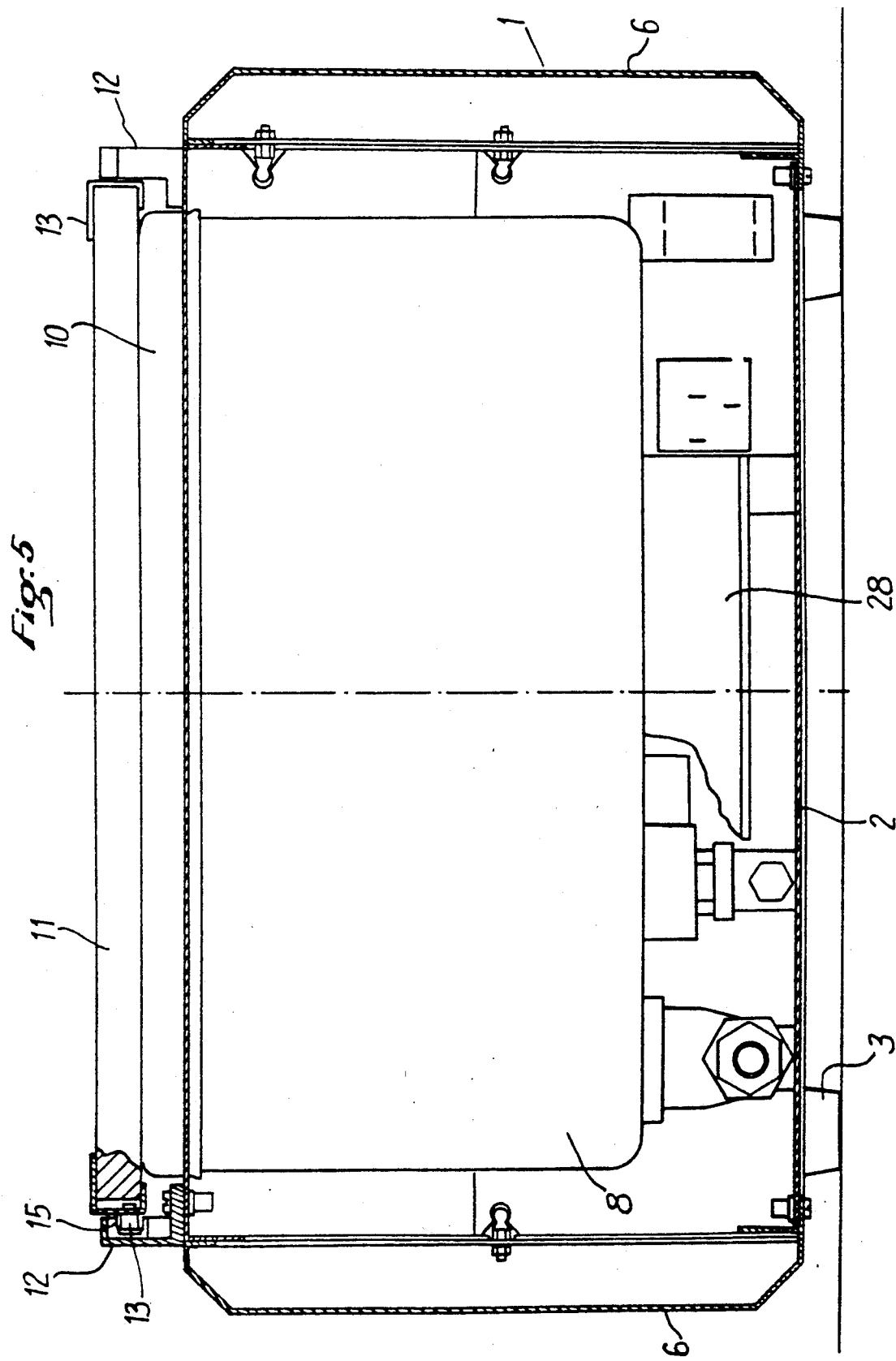

CENTRIFUGAL EVAPORATOR-CONCENTRATOR FOR CONCENTRATING SPECIMENS BY EVAPORATION OF THE SOLVENT

This is a division of application Ser. No. 07/492,101 filed Mar. 12, 1990 now U.S. Pat. No. 5,084,133, issued Jan. 28, 1992.

The present invention relates to a process for concentrating specimens, for example biochemical specimens, by evaporation of the solvent. The process employs a centrifugal evaporator-concentrator of the type comprising an inside enclosure in the form of a vessel in which a vacuum is established, a specimen-carrying rotor which is driven in rotation so as to apply the specimen solution by centrifugal effect against the inner end of its container placed in the rotor, an a means for discharging the vapours of the solvent which are given off by the specimens to be concentrated.

In these known apparatuses, the evaporation procedure is accelerated by the creation of the partial vacuum which lowers the temperature of the boiling point of the liquid solution of the specimen. A heating by radiation from a source of heat outside the vessel permits simultaneously transferring of heat to the specimens to be concentrated. The centrifugal effect applied to the specimens avoids splashing in the event of a boiling of the solutions in their container or test tube.

A suction orifice inside the vessel is connected to a pump which puts the vessel under vacuum and also draws off the solvent vapours.

Centrifugal evaporators-concentrators of this type are described in the patents U.S. Pat. Nos. 3,304,990 and 4,226,669. The main drawback of these known apparatuses resides in the relatively long duration of the concentration cycle.

An object of the invention is to overcome this drawback and to provide a process for concentrating by evaporation of solvent in centrifugal evaporators-concentrators which markedly reduces the duration of the evaporation.

Another object of the invention is to provide a centrifugal evaporator-concentrator for carrying out said process.

Another object of the invention is to provide such a centrifugal concentrator-evaporator in which the heating of the specimens to be concentrated can be ensured in a much more rapid and in a much better controlled manner during the operation of the apparatus.

A further object of the invention is to provide a centrifugal evaporator-concentrator in which a regular and homogeneous circulation of the flows of gas and vapour which must be extracted from the enclosure can be established.

Yet another object of the invention is to so arrange such a centrifugal evaporator-concentrator that the number of rotating elements is reduced.

A further object of the invention is to provide such a centrifugal evaporator-concentrator whose overall size is particularly reduced.

The invention provides a process for concentrating by evaporation of solvent in a centrifugal evaporator-concentrator. The process comprises, after having put the containers such as tubes or test tubes containing the specimen solution to be concentrated in the initially stationary rotor of the evaporator-concentrator, establishing in the enclosure containing the rotor a partial vacuum which lowers the boiling point of the solvent. The rotor is the driven in rotation while discharging by suction the solvent vapours formed. The process further comprises temporarily admitting into the enclosure a gas, such as air; By imparting to said gas sufficient temperature, the gas transmits heat to the specimens to be concentrated. The gas is then discharged.

The sequence of admission and discharge of the gas such as air in the enclosure is repeated a number of times and preferably periodically during the operation of the apparatus.

The gas such as air admitted into the enclosure according to the process of the invention may, if desired, be brought to a sufficiently high temperature before it is introduced into the enclosure.

However, it is preferred to heat the gas inside the enclosure preferably by means of a source of heat inside the enclosure. Furthermore, the radiation of said source also supplies heat to the specimens.

It will be understood that, by means of the invention, there is achieved a true sweeping over the rotor and in particular the specimens by the gas temporarily and periodically admitted into the enclosure. It then possible for the gas to communicate heat, by conduction and convection, to the specimens and thereby accelerate the evaporation and reduce the total duration of the concentration cycle.

Between two consecutive admissions of gas into the enclosure, the partial vacuum is completely re-established in the latter.

For apparatuses in which there is established in normal operation a vacuum on the order of 1 hpa (hectopascal) inside the enclosure in which the rotor rotates, the maximum pressure prevailing in the enclosure at the moment of admitting the gas is preferably between 50 and 500 hpa.

The duration of a sequence comprising the admission of the gas, the optional maintenance in the enclosure, and then the discharge of the gas, is relatively short. For example, the admission of gas lasts on the order of 0.5 to 20 s seconds, the rate of discharge depending on the performances of the vacuum pump and being generally longer than the duration of the admission period. The gas could, if desired, be maintained in the enclosure for a certain period, for example 1 to 20 s, before extracting it. These sweeping sequences are preferred to be carried out with a frequency on the order of 10 to 60 sequences per hour.

The temperature in the enclosure is preferably on the order of 40° C.

In a particularly advantageous manner, in accordance with an improvement of the invention, the gas such as air may be admitted and then discharged through a central orifice located in the region of the axis of rotation of the rotor of the centrifugal evaporator-concentrator. The same orifice advantageously serves to establish the vacuum and to discharge the solvent vapours by suction. There is achieved in this way a particularly regular sweeping of gas owing to the center of symmetry thus obtained.

The invention also provides a centrifugal evaporator-concentrator for carrying out said process, which comprises means for admitting and discharging a gas such as air in the enclosure in accordance with a desired sequence and the required number of times, and then discharging said gas.

In a particularly advantageous embodiment of this apparatus, the orifice is placed on the vertical axis of rotation of the rotor in the vessel forming the enclosure.

Preferably, this orifice is constituted by the end of a tube extending into the vessel forming the enclosure, through the bottom of the latter, and this tube constitutes the pivot about which the rotor rotates. In this embodiment, it is also preferred that a source of heat, for example an infrared ray element disposed in facing relation to the orifice, heat the gas which issues from the orifice. Preferably, this is done under the cover closing the vessel in a sealed manner, so that the gas is rapidly heated and directed toward the tubes or test tubes placed in the rotor.

The invention therefore also provides a centrifugal evaporator-concentrator devoid of means for sweeping according to the preceding process, but comprising said orifice placed on the vertical axis of rotation of the rotor. It is then easy to arrange this centrifugal evaporator-concentrator by mounting on a nozzle connected to said orifice the aforementioned means for admitting and discharging the gas in accordance with the desired sequences.

The orifice is connected to a pump creating the vacuum and it is preferred to connect this orifice, through a suitable nozzle, to a three-way electrically operated valve. The second way of the valve leads to the vacuum pump and the third way in particular, is open. This permits on the one hand, the connection to the atmospheric pressure and, on the other hand, the admission of the required limited quantity of air for the sweeping effect according to the process of the invention.

This three-way electrically operated valve may be replaced by two-way electrically operated valves, one being placed in the way leading to the vacuum pump and the other in the way of the source of sweeping gas (for example the atmosphere) by controlling these valves in accordance with any desired sequence.

However, it is also possible to employ a normally-open two-way electrically operated valve which ensures the creation of atmospheric pressure by acting on a control for starting up and stopping the pump.

In a particularly advantageous embodiment of the invention, the rotor is driven in rotation by mounting on the rotor in the lower part thereof a magnetized element, for example a magnetized disk or ring having an alternation of north poles and south poles on its side in facing relation to the bottom of the enclosure. This element cooperates with coils supplied with current and located outside the enclosure and faces toward the magnetized element for the purpose of creating a rotating field ensuring the rotation of the magnetized element and therefore the rotor.

Preferably, sensors, such as Hall-effect sensors, detect the angular position of the magnetized element relative to the exciting coils and control the commutation of the direction of circulation of the electric current in the various coils so as to bring about alternately the attraction or the repulsion of the magnetic pole located in their respective field of action.

With this arrangement, any rotating element outside the enclosure is eliminated and the coils may have a relatively small height so that the vertical overall size of the apparatus can be markedly reduced.

The cover, preferably made from a transparent material such as; glass, serves to hermetically close the vessel and constitutes the enclosure in which the rotor rotates; cooperates. This cover preferably with locking means for locking the cover right at the start of the operation of the apparatus; In addition. A means responsive to the speed of rotation of the rotor being provided for unlocking the locking means when the speed of the rotor becomes zero or low. It is then impossible to proceed to the opening of the cover during the operation of the apparatus owing to the mechanical locking thereof.

A suitable sensor advantageously detects the normally-closed position of the cover so as to permit the starting up of the apparatus only when the cover is in the closed position.

Further features and advantages of the invention will be apparent from the following description, given as a non-limitative example, with reference to the accompanying drawing in which:

FIG. 3 is a horizontal sectional view just below the base of the vessel;

FIG. 4 is a front view of the concentrator;

FIG. 5 is a view similar to FIG. 4, the front part of the casing having been removed.

Figure 1:
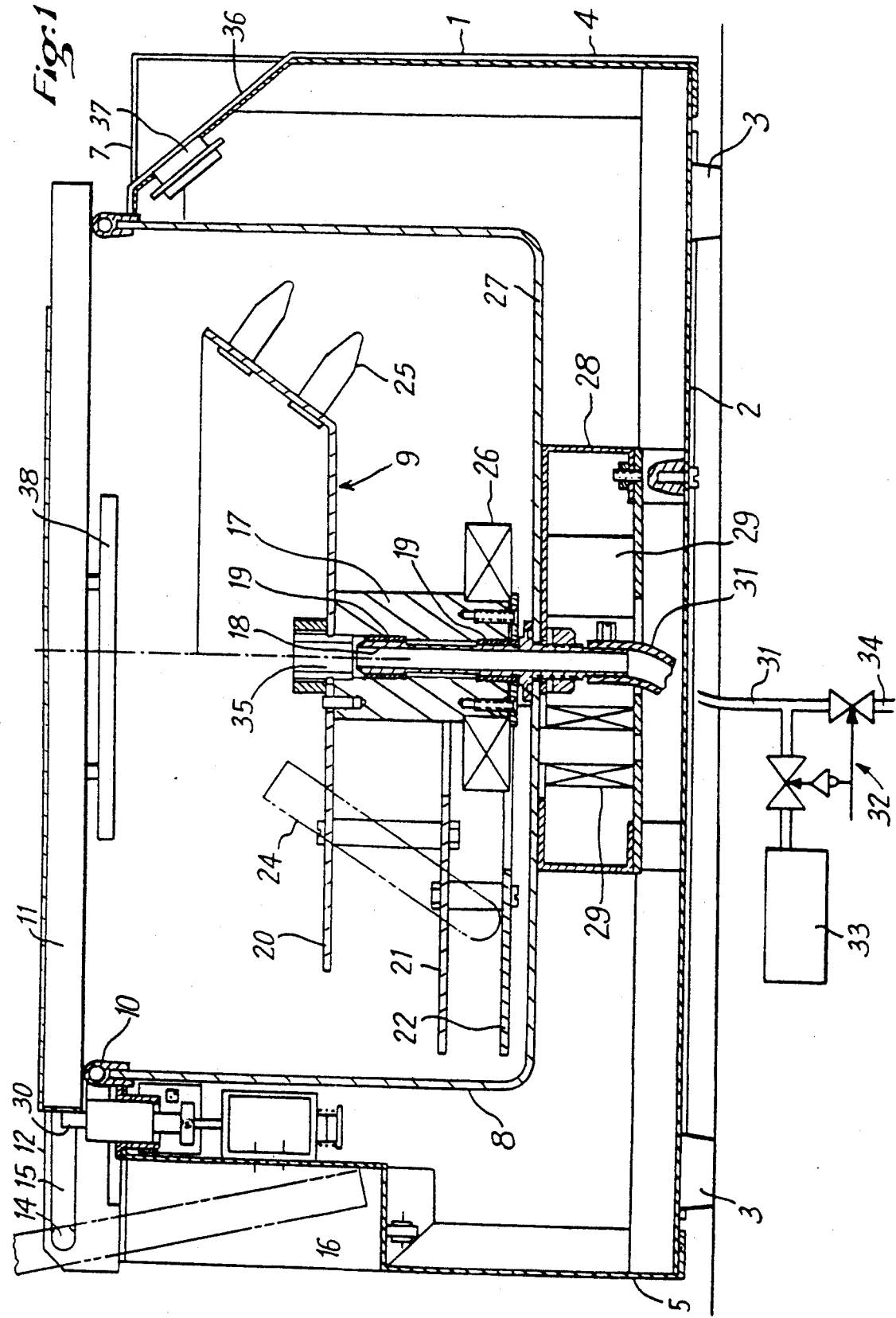
FIG. 1 is a vertical sectional view, in the direction from the front to the rear, of the centrifugal evaporator-concentrator according to the invention.

The illustrated centrifugal evaporator-concentrator comprises a casing or cowling 1 with a base 2, feet 3, a front edge 4, a rear edge 5, two lateral sides 6, and an upper side 7 defining a large circular opening. Extending this circular opening through the upper edge portion of a cylindrical vessel 8 composed of non-magnetic stainless steel in which a rotor 9 rotates. The opening edge of the vessel 8 forming a hermetic enclosure is surrounded by a sealing element 10 against which is applicable a cover 11 made from thick glass. This cover is guided and maintained in position by two horizontal lateral rails 12. More precisely, the cover 11, of rectangular shape, presents front projections 13 and rear projections 14 constituting axes about which rotate rollers which run in openings 15 in the rails 12. The cover 11 can therefore be guided in horizontal translation in the rails between a closing position represented in FIG. 1 and a releasing position in which the rear projections 14 abut against the ends of the rails 15. Thus, the cover, when it reaches this position, is pivotable about the axis defined by the projections 14, the projections 13 being capable at this moment of escaping from the rails 12 through suitably disposed gaps in the upper edge of the rails 12.

It can therefore be seen that the part of the cover 11 to the rear of the projections 14 is capable of placing itself in the pivoted position in a recess 16 in the rear side 5 of the casing 1 so that the overall size of the apparatus is reduced.

Figure 2:
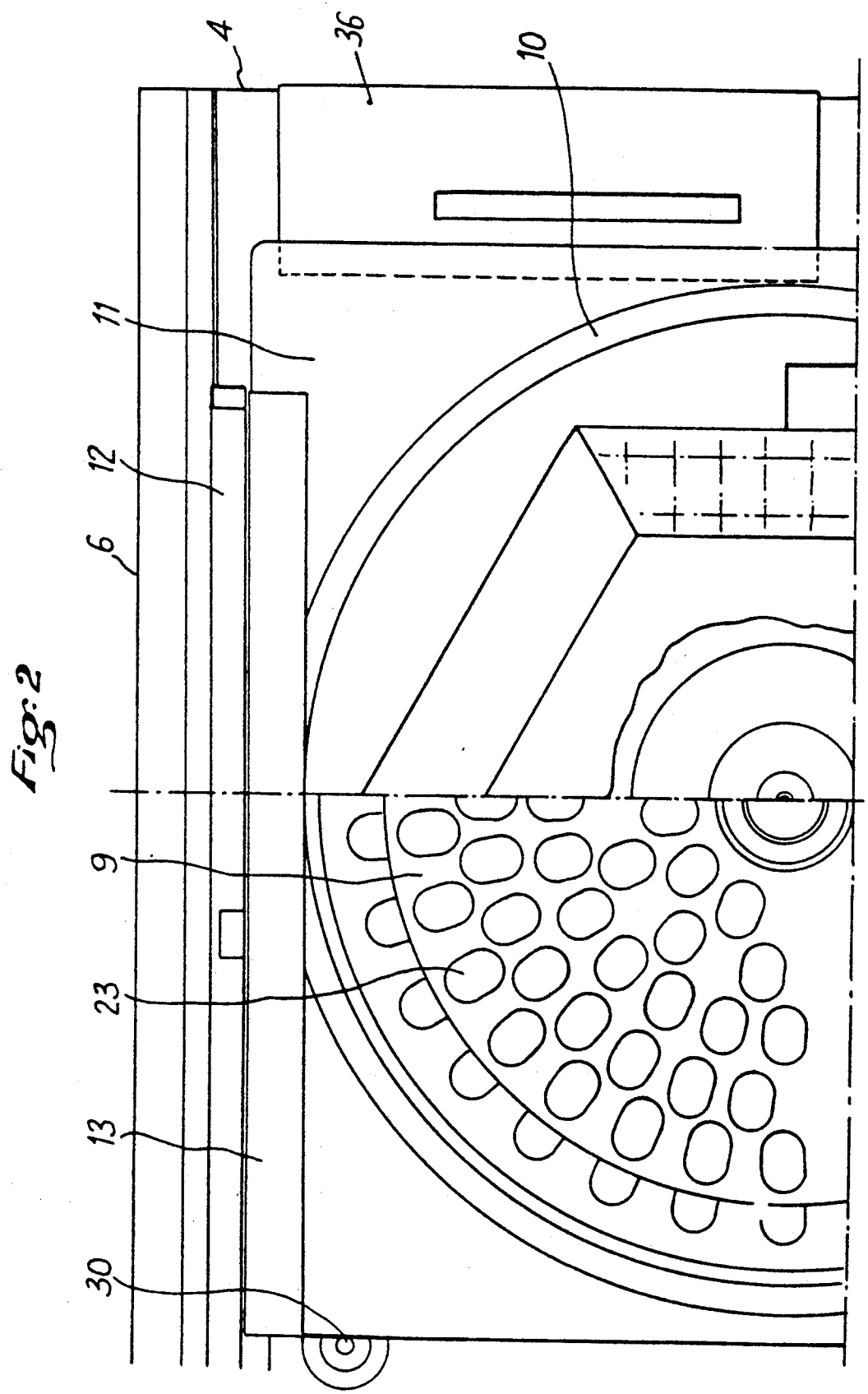
FIG. 2 is a top plan view of this concentrator.

The rotor 9 comprises a hub 17 which is pivotal about a vertical tubular pivot 18 with interposition of self-lubricating bushes 19. The lower bush 19 is mounted on a horizontal circular fixed bearing surface so as to maintain the rotor in a vertical position. The hub of the rotor carries a number of plates 20, 21, 22, defining, as shown in FIG. 2, oblong openings 23 all disposed in the conventional manner for receiving in an inclined position specimen-carrying test tubes 24,25. This arrangement of the plates is conventional and will not be described in more detail.

In its lower part, the hub 17 carries an annular element 26 having an alternation of north poles and south poles oriented toward the bottom 27 of the vessel 8 which is disposed in proximity thereto. Preferably, the annular element 26 has three north poles and three south poles.

Housed under the bottom 27 of the vessel 8 is an electromagnetic driving unit 28 comprising four fixed coils 29 for receiving current from an electric network through a distributor having a transistorized commutation of conventional type. This permits the selective and successive control of the four coils in the desired direction of rotation of the field. Two Hall-effect sensors (not shown) are also disposed in this region so as to be responsive to the poles of the magnetized element 26, and consequently to the angular position of the rotor and preferably also to its speed. The sensors control the commutation means in the known manner so as to ensure the commutation in the direction of circulation of the current in each coil and thereby produce alternately an attraction or a repulsion of the magnetic pole located in the field of action of the coil concerned. This results in a rotation of the rotor at the required speed, on the order of 1500 rpm. It will be understood that, as the coils 29 are vertically very thin, there is obtained, for a normal vessel height and rotor height, a vertical overall size of the apparatus which is considerably reduced.

In order to ensure the locking of the cover, a slidable pin 30 driven by a suitable magnetic coil is placed behind the rear edge of the cover 11 when the latter is in the closing position and the apparatus is started up. The pin 30 in this way blocks the cover in position so that it cannot move rearwardly, the cover being moreover prevented from moving in the forward direction by a suitable abutment of the cover against the front end of the rails 12. Furthermore, a sensor permits checking the correct closure of the cover before allowing the rotation of the rotor.

For safety reasons, when the apparatus is stationary, the supply of current to the coil maintaining the pin 30 in its upper blocking position is subordinate to the detection of the speed of rotation of the rotor 9. It is thus possible to detect this speed, for example by means of Hall-effect sensors, so that the pin 30 remains in its locking position so long as the speed of the rotor has not become substantially zero.

The tubular pivot 18 extends through the bottom 27 of the vessel in a sealed manner owing to the provision of an O-ring, and further extends through the inside of the unit 28 where it is connected to a flexible tube 31 leading to a three-way electrically operated valve system 32. Valve system 32 leads, through one of the ways, to the vacuum pump 33 with optionally interposition of elements such as solvent traps and acid traps, and through another way 34 to the air of the atmosphere. When the way 34 is open, it enables the interior of the vessel to be put at atmospheric pressure by means of the orifice or nozzle 35 through which the tubular pivot opens into the vessel. If the way 34 is closed and the way leading to the vacuum pump 33 is open, the latter establishes in the enclosure formed by the vessel the required partial vacuum. The driving means of the vacuum pump 33 may be advantageously activated by a relay beyond a certain speed of the rotor, for example 600 rpm, and released if the speed of the rotor drops below 500 rpm.

The illustrated centrifugal evaporator-concentrator may be advantageously controlled by means of a conventional control panel 36 having conventional keys which control a microprocessor 37 performing the apparatus control functions.

A heating resistor 38 is carried by the lower side of the cover 11 and is suitably supplied with power from the exterior of the cover through conductors extending through the cover.

The microprocessor manages in particular the following functions:
the general electric supply of the apparatus,
sensing the position of the cover,
positioning the locking pin,
supplying current to the coils,
detecting the speed of the rotor,
heating by means of the resistor,
starting up and stopping the vacuum pump and,
actuation of the electrically operated valve or valves.

The user programs on the keyboard 37 the duration of a cycle of operation of the apparatus in accordance with the volumes and the types of the solvents of the specimens to be evaporated. The duration of this cycle of operation is for example programmable between 1 and 999 min. The STOP key, however, permits manually stopping the apparatus at any moment. The user also programs by means of the keyboard the intensity of the thermal heating of the resistor 38 by the programmation of the electric power consumed. The user moreover decides by means of the control panel 37 if the operation will be carried out with or without a periodical sweeping or scavenging with air.

The test tubes containing the specimens having been placed in the rotor, the user closes the cover 11 and depresses a START key. In the event of a bad position of the cover 11, the sensor detecting the position of the cover prevents the starting up of the cycle. If the starting up is allowed, the pin 30 is urged upwardly and blocks the cover 11 in position. At this moment, the coils 29 are supplied with current and the rotor starts to rotate with increasing speed. When the speed exceeds the threshold of 600 rpm, the vacuum pump 33 is actuated by the microprocessor. Then the electrically operated valve closes the opening 34 and, on the other hand, opens the way leading to the vacuum pump 33 which rapidly establishes the partial vacuum (1 hpa) in the enclosure 8. During this time, supply of current to the resistor 38 has begin in accordance with the program. The rotor finally reaches its normal speed of 1500 rpm which is maintained up to the end of the cycle. When the cycle reaches its end, the supply of current to the coils 29 is reversed so as to brake the rotor. Likewise, the supply of current to the resistor 38 is stopped. When the speed of rotation of the rotor 19 passes through the threshold of 500 rpm, the pump relay is put out of action and the vacuum pump ceases to operate. At this moment, the electrically operated valve 32 opens the way 34 and the air of the atmosphere is able to enter the vessel until equality between the pressures is achieved. It will moreover be noted that the electrically operated valve 32 is adapted in such manner that, in the event of the current being cut off, the way 34 is normally open in order to avoid projections of solvent in the event of the stoppage of the rotor. When the speed of the rotor becomes very low, on the order of a few rpm, the detection of this low speed causes the locking pin 30 to be downwardly withdrawn so that the cover may be opened.

It will be understood that, when establishing a vacuum, the air initially contained in the vessel is drawn off through the orifice 35 in the central position and this homogenizes the distribution of the air flows in the enclosure. Furthermore, vapours are then drawn off through the orifice 35 and may be discharged with the highest efficiency.

When the user has programmed the sweeping in accordance with the process of the invention, this sweeping is carried out in the following manner: the required vacuum having been established and being maintained by the vacuum pump 33, the way 34 is closed. At the moment the sweeping sequence starts, the electrically operated valve 32 changes the way, the vacuum pump 33 is isolated and the way 34 is opened for a short instant. A small quantity of air may then penetrate through the pipe 31 into the enclosure, this quantity of air being determined by the programmed duration of the opening of the way 34, for example on the order of a few seconds. The air which enters the enclosure axially issues therefrom through the nozzle 35 and is preferably projected toward the resistor 38 where it is rapidly heated and from there distributed in an angularly uniform manner throughout the enclosure where it heats by conduction the specimens in their test tubes 24, 25. When the desired volume of air has been admitted, the way 34 is closed again and the way leading to the vacuum pump is opened so that the air and the vapours which are given off are drawn off in the opposite direction through the orifice 35 and discharged. It is of course also possible to employ two two-way electrically operated valves so as to allow a certain lapse of time between the closing of the way 34 and the opening of the way leading to the pump 33 and to allow the rotor to rotate during this time in the volume of sweeping air admitted.

The total duration of the sweeping sequence is preferably on the order of a few seconds to a few tens of seconds and the frequency of these sequences is preferably on the order of 10 to 60 per hour.

Owing to this sweeping, the total cycle of operation of the apparatus may be reduced on the order of 10% to 60%, depending on the case.

It must be understood that the apparatus of the invention may be subjected to various modifications. It may first of all be simplified and the microprocessor 37 may if desired be eliminated so as to carry out the operations by a manual actuation. In this case, a two-way valve may be employed, the branch connection leading to the vacuum pump 33 always remaining open.

What is claimed is:

1. Centrifugal evaporator-concentrator for concentrating a specimen by evaporation of a solvent from a specimen solution, comprising:
   an enclosure,
   a rotor which is rotatable in the enclosure and including a holding means for holding the specimen solution,
   a driving means for rotating said rotor,
   an admitting means for admitting gas into the enclosure,
   a heating means for heating the gas admitted to the enclosure by said admitting means,
   an extracting means for extracting said gas from the enclosure, and
   a control means for controlling said admitting means and said extracting means according to a desired sequence and a desired number of times whereby the admitting and extracting of the gas effect a concentration of the specimen by evaporation of the solvent in the specimen solution contained in said holding means.

2. Centrifugal evaporator-concentrator according to claim 1, wherein said admitting means for admitting gas into the enclosure and said extracting means for extracting said gas include a common opening in said enclosure.

3. Centrifugal evaporator-concentrator according to claim 2, wherein said opening is located on a vertical axis about which the rotor rotates in the enclosure.

4. Centrifugal evaporator-concentrator comprising:
   an enclosure in which a vacuum can be established,
   a centrifugal rotor mounted in the enclosure to be rotatable about a vertical axis,
   a driving means for rotating said rotor,
   an access means defining an opening for admitting gas and extracting the gas and vapours produced in the enclosure along said vertical axis of rotation of the rotor,
   an admitting means connected to said access means defining an opening for admitting gas into the enclosure,
   a heating means for heating the gas admitted to the enclosure by said admitting means,
   an extracting means for thereafter extracting said gas according to a desired sequence and a desired number of times, and
   a control means for controlling said admitting means and said extracting means according to a desired sequence and a desired number of times.

5. Centrifugal evaporator-concentrator according to claim 4, wherein said means defining an opening is a nozzle.

6. Centrifugal evaporator-concentrator according to claim 3, wherein said enclosure includes a bottom wall and said opening comprises an end of a tube extending into the enclosure through said bottom wall, said tube constituting a pivot defining said axis about which the rotor rotates.

7. Centrifugal evaporator-concentrator according to claim 1, further comprising a cover for closing the enclosure and wherein said heating means is a resistance heater under said cover.

8. Centrifugal evaporator-concentrator according to claim 1, wherein the enclosure includes a bottom wall; wherein the driving means comprises (a) in a lower part of the rotor a magnetized element comprising on a side thereof in facing relation to said bottom wall an alternating arrangement of north poles and south poles, and (b) electric coils cooperative with said magnetized element and located outside the enclosure in alignment with said magnetized element for creating a rotating field for the purpose of rotating the magnetized element and the rotor.

9. Centrifugal evaporator-concentrator according to claim 8, wherein said control means comprises sensors for detecting the relative position between said magnetized element and said coils and a commutator means for controlling a commutation of the direction of electric circulations so as to cause alternately the attraction and the repulsion of the magnetic poles located in their respective fields of action.

10. Centrifugal evaporator-concentrator according to claim 2, wherein said extracting means includes a vacuum pump, and wherein said control means includes a three-way electrically operated valve for connecting said opening selectively to the atmosphere and to the vacuum pump.

11. Centrifugal evaporator-concentrator according to claim 1, further comprising a cover for the enclosure, a locking means for locking the cover right at a start of rotation of the rotor, and a release means responsive to a speed of rotation of the rotor and cooperative with the locking means for releasing the locking means when the speed of rotation of the rotor becomes substantially zero.

12. Centrifugal evaporator-concentrator according to claim 11, comprising a sensor means associated with the cover for detecting a normally-closed position of the cover and allowing the starting up of the rotor only when the cover is in the closed position.

13. Centrifugal evaporator-concentrator according to claim 11, comprising rails cooperative with the cover for guiding the cover in translation in a horizontal plane to a releasing position of the cover, means for rendering the cover pivotable in said releasing position about an axis, said axis about which the cover is pivotable being defined by pivots located in an intermediate position on the cover so as to reduce the overall size of the centrifugal evaporator-concentrator in the opening position of the cover.

14. Centrifugal evaporator-concentrator according to claim 1, wherein said control means further comprises an actuating keyboard, a microprocessor connected to the keyboard for programming and carrying out a cycle of operation of the centrifugal evaporator-concentrator, which cycle of operation includes a heating and a sweeping effected by the gas and by the admission and extraction of the gas.

* * * * *